United States Patent
Vanderwalde et al.

(10) Patent No.: US 10,034,938 B2
(45) Date of Patent: Jul. 31, 2018

(54) METHOD FOR TREATING MELANOMA USING A HERPES SIMPLEX VIRUS AND AN IMMUNE CHECKPOINT INHIBITOR

(71) Applicant: AMGEN INC., Thousand Oaks, CA (US)

(72) Inventors: Ari Vanderwalde, Memphis, TN (US); Mohamed Shabooti, Agoura Hills, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 14/424,424

(22) PCT Filed: Aug. 30, 2013

(86) PCT No.: PCT/US2013/057542
§ 371 (c)(1),
(2) Date: Feb. 26, 2015

(87) PCT Pub. No.: WO2014/036412
PCT Pub. Date: Mar. 6, 2014

(65) Prior Publication Data
US 2015/0202290 A1  Jul. 23, 2015

Related U.S. Application Data

(60) Provisional application No. 61/846,147, filed on Jul. 15, 2013, provisional application No. 61/694,963, filed on Aug. 30, 2012.

(51) Int. Cl.
| | |
|---|---|
| A61K 39/395 | (2006.01) |
| A61K 35/763 | (2015.01) |
| C07K 14/535 | (2006.01) |
| C07K 16/28 | (2006.01) |
| A61K 39/00 | (2006.01) |
| A61K 31/00 | (2006.01) |

(52) U.S. Cl.
CPC ...... *A61K 39/39558* (2013.01); *A61K 35/763* (2013.01); *A61K 39/3955* (2013.01); *C07K 14/535* (2013.01); *C07K 16/2818* (2013.01); *A61K 2039/505* (2013.01); *A61K 2039/525* (2013.01); *C07K 2317/21* (2013.01); *C07K 2317/76* (2013.01); *C12N 2750/14343* (2013.01); *C12N 2799/025* (2013.01)

(58) Field of Classification Search
CPC .......... A61K 2300/00; A61K 2039/505; A61K 39/0011; A61K 35/768; A61K 35/763; A61K 38/1774; A61K 39/245; A61K 2039/525; A61K 2039/5256; A61K 39/00; A61K 39/12; C07K 2317/56; C07K 2317/51; C07K 2317/515; C07K 14/70503; C07K 2317/55; C07K 14/4748; C07K 16/00; C07K 14/005; C12N 7/00; C12N 2710/16021; C12N 2710/16034; C12N 15/86; C12N 2710/16633; C12N 2710/16641
See application file for complete search history.

(56) References Cited

U.S. PATENT DOCUMENTS

| | | | |
|---|---|---|---|
| 7,223,593 B2 * | 5/2007 | Coffin | A61K 35/763 424/93.2 |
| 7,488,802 B2 | 2/2009 | Collins et al. | |
| 7,537,924 B2 | 5/2009 | Coffin | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 8,277,818 B2 * | 10/2012 | Coffin | A61K 35/763 424/199.1 |
| 8,680,068 B2 * | 3/2014 | Coffin | A61K 35/763 424/199.1 |
| 2009/0220460 A1 * | 9/2009 | Coffin | A61K 35/763 424/93.6 |
| 2011/0118464 A1 * | 5/2011 | Chen | C07D 295/073 544/272 |
| 2012/0263677 A1 * | 10/2012 | Eagle | A61K 38/193 424/85.2 |
| 2014/0154215 A1 * | 6/2014 | Coffin | A61K 35/763 424/93.2 |
| 2014/0377221 A1 * | 12/2014 | Tufaro | G01N 33/57484 424/85.2 |

FOREIGN PATENT DOCUMENTS

| | | | | |
|---|---|---|---|---|
| CN | 1425073 A | 6/2003 | | |
| EP | 2591796 A1 * | 5/2013 | ........... | A61K 38/208 |
| EP | 2890714 A2 | 7/2015 | | |
| WO | 2001-053506 A2 | 7/2001 | | |
| WO | 2003-042402 A2 | 5/2003 | | |
| WO | 2008-156712 A2 | 12/2008 | | |
| WO | 2010-036959 A2 | 4/2010 | | |
| WO | 2010-089411 A2 | 8/2010 | | |

(Continued)

OTHER PUBLICATIONS

Russell SJ, Peng KW, Bell JC. Oncolytic virotherapy. Nat Biotechnol. Jul. 10, 2012;30(7):658-70. Published online Jul. 10, 2012.*
(American Cancer Society. Melanoma Skin Cancer: How is Melanoma Skin Cancer Staged? http://www.cancer.org/cancer/skincancer-melanoma/detailedguide/melanoma-skin-cancer-staging. Revised Feb. 1, 2016.*
IPILIMUMAB: Trademark details. Bristol-Myers Squibb, Co.; U.S. Appl. No. 77/273,787, filed Sep. 7, 2007.*
Sivendran S, Pan M, Kaufman HL, Saenger Y. Herpes simplex virus oncolytic vaccine therapy in melanoma. Expert Opin Biol Ther. Jul. 2010;10(7):1145-53.*

(Continued)

*Primary Examiner* — Rachel B Gill
(74) *Attorney, Agent, or Firm* — Raymond M. Doss

(57) ABSTRACT

The invention relates to methods of treating melanoma using a herpes simplex virus in combination with an immune checkpoint inhibitor.

19 Claims, No Drawings

(56) References Cited

FOREIGN PATENT DOCUMENTS

| WO | 2011-066342 A2 | 6/2011 |
| --- | --- | --- |
| WO | 2011-082400 A2 | 7/2011 |
| WO | 2011-159877 A2 | 12/2011 |
| WO | 2011-161699 A2 | 12/2011 |
| WO | WO2014/036412 A2 | 3/2014 |

OTHER PUBLICATIONS

Zhang W, Fulci G, Buhrman JS, Stemmer-Rachamimov AO, Chen JW, Wojtkiewicz GR, Weissleder R, Rabkin SD, Martuza RL. Bevacizumab with angiostatin-armed oHSV increases antiangiogenesis and decreases bevacizumab-induced invasion in U87 glioma. Mol Ther. Jan. 2012;20(1):37-45.*

Eshun FK, Currier MA, Gillespie RA, Fitzpatrick JL, Baird WH, Cripe TP. VEGF blockade decreases the tumor uptake of systemic oncolytic herpes virus but enhances therapeutic efficacy when given after virotherapy. Gene Ther. Jul. 2010;17(7):922-9.*

Zhu Y, Jin K, Mao XO, Greenberg DA. Vascular endothelial growth factor promotes proliferation of cortical neuron precursors by regulating E2F expression. FASEB J. Feb. 2003;17(2):186-93.*

Kimura I, Honda R, Okai H, Okabe M. Vascular endothelial growth factor promotes cell-cycle transition from G0 to G1 phase in subcultured endothelial cells of diabetic rat thoracic aorta. Jpn J Pharmacol. May 2008;83(1):47-55.*

Batch et al "Final Version of 2009 AJCC Melanoma Staging and Classification," *Journal of Clinical Oncology*, Dec. 2009, 27(36): 6199-6206.

Blois et al, "Malignant melanoma of the skin" *Cancer*, Oct. 1983, 52(7): 1330-1341.

Clark, W. et al, "Model predicting survival in stage 1 melanoma based on tumor progression," *Journal of National Cancer Institute*, Dec. 1989, 81(24): 1893-1904.

Fong, L. et al, "Potentiating Endogenous Antitumor Immunity to Prostate Cancer through Combination Immunotherapy with CTLA4 and Blockade and GM-CSF," *Cancer Research*, Jan. 2009, 69(2): 609-615.

Harrington, K. et al, "Phase I Study of Lapatinib in Combination With Chemoradiation in Patients With Locally Advanced Squamous Cell Carcinoma of the Head and Neck," American Society of Clinical Oncology, Mar. 2009, 27(7): 1100-1107.

Hodi, F.S et al, "Improved Survival with Ipilimumab in Patients with Metastatic Melanoma," *The New England Journal of Medicine*, Aug. 2010, 363(8): 711-723.

Hu, J. et al, "A Phase I Study of OncoVEXGM-CSF, a Second-Generation Oncolytic Herpes Simplex Virus Expressing Granulocyte Macrophage Colony-Stimulating Factor," *Clinical cancer research* (American Association for Cancer Research), Nov. 2006, 12(22): 6737-6747.

Hunter, W.D. et al, "Attenuated, replication-competent herpes simplex virus type 1 mutant G207: safety evaluation of intracerebral injection in nonhuman primates," *Journal of Virology*, Aug. 1999, 73(8): 6319-6326.

Jemal, A., et al, "Cancer Statistics," *CA Cancer J. Clin*. 2006, 56(2): 106-130.

Kapadia, D. et al, "CTLA-4 blockade: autoimmunity as treatment," *Journal of Clinical Oncology*, Dec. 2005, 23(35): 8926-8928.

Karakousis et al, "Predictors of Regional Nodal Disease in Patients With Thin Melanomas," *Annals of Surgical Oncology*, Apr. 2006, 13(4): 533-541.

Kaufman, H. et al, "Local and Distant Immunity Induced by Intralesional Vaccination with an Oncolytic Herpes Virus Encoding GM-CSF in Patients with Stage IIIc and IV Melanoma," *Annals of Surgical Oncology*, Springer-Verlag, NE, Published online Nov. 14, 2009, 17(3): 718-730.

Kaufman, H.L. et al, "OPTIM trial: a Phase III trial of an oncolytic herpes virus encoding GM-CSF for unresectable stage III or IV melanoma," *Future oncology*, 6(6): 941-949, Jun. 2010.

Koh, H.K., "Cutaneous melanoma" NEMJ.org, Jul. 1991, 325(3)::171-82.

Leon et al, "The Prognostic Implications of Microscopic Satellites in Patients with Clinical Stage 1 Melanoma," *Archives of Surgery*, Dec. 1991, 126(2): 1461-1468.

Liu, B. et al, "ICP34.5 deleted herpes simplex virus with enhanced oncolytic, immune stimulating, and anti-tumour properties." *Gene Therapy, Nature P:ublishing Group*, GB, Feb. 2003; 10(4) : 292-303.

Loo et al, "Development of an Fc-Enhanced Anti-B7-H3 Monoclonal Antibody with Potent Antitumor Activity," *Clinical Cancer Research*, Jul. 2012, 18(14): 3834-3845.

MacKie, R.M. et al, "Intralesional injection of herpes simplex virus 1716 in metastatic melanoma," *The Lancet*. Feb. 2001, 357(9255): 525-526.

Markert, J.M. et al, "Conditionally replicating herpes simplex virus mutant, G207 for the treatment of malignant glioma: results of a phase I trial," *Gene Therapy*, May 2000, 7(10): 867-874.

Overett, T.K. et al, "Surgical treatment of distant metastatic melanoma indications and results," *Cancer*, Sep. 1985, 56(5): 1222-1230.

Pardoll, D., "The blockade of immune checkpoints in cancer immunotherapy," www.nature.com/reviews/cancer, Apr. 2012, vol. 12: 252-264.

Quesada, S. et al, "CTLA4 blockade and GM-CSF combination immunotherapy alters the intratumor balance of effector and regulatory T cells," *J Clin Invest*. Jul. 3, 2006; 116(7): 1935-1945.

Rampling, R. et al, "Toxicity evaluation of replication-competent herpes simplex virus (ICP 34:5 null mutant 1716) in patients with recurrent malignant glioma," *Gene Therapy*, May 7, 2000(10): 859-866.

Ries, L. et al, "The annual report to the nation on the status of cancer, 1973-1997, with a special section on colorectal cancer," *Cancer*, May 2000, 88(10): 2398-2424.

Robert, C. et al, "Ipilimumab plus Decarbazine for Previously Untreated Metastatic Melanoma," The New England Journal of Medicine, Jun. 2011, 364(26): 2517-2526.

Senzer, N. et al, "Phase II Clinical Trial of a Granulocyte-Macrophage Colony-Stimulating Factor-Encoding, Second-Generation Oncolytic Herpesvirus in Patients With Unresectable Metastatic Melanoma," *Journal of Clinical Oncology*, Dec. 2009, 27(34): 5763-5771.

Shumate, C. R. et al, "The Prognostic Implications of Location for Scalp Melanoma," *The American Journal of Surgery*, Oct. 1991, 162(4): 315-319.

Siegel, R. et al, "Cancer Statistics," *CA Cancer J. Clin*, 2012, 62(1): 10-29.

Sivendran, S. et al, "Melanoma Immunotherapy," *Mount Sinai Journal of Medicine: A Journal of Translational and Personalized Medicine*, Published online Nov. 23, 2010, vol. 77: 620-642. Abstract.

Slinguff, C. et al, "The Annual Risk of Melanoma Progression," *Cancer*, Mar. 1992, 70(7): 1917-1927.

Sundaresan, P. et al, "Attenuated, replication-competent herpes simplex virus type 1 mutant G207: safety evaluation in mice," *Journal of Virology*, Apr. 2000, 74(8): 3832-3841.

Van Elsas et al, "Combination Immunotherapy of B16 Melanoma Using Anti-Cytotoxic T Lymphocyte-Associated Antigen 4 (Ctla-4) and Granulocyte/Macrophage Colony-Stimulating Factor (Gm-Csf)-Producing Vaccines Induces Rejection of Subcutaneous and Metastic Tumors Accompanied by Autoimmune Depigmentation," *Journal of Experimental Medicine*. Aug. 2, 1999; 190(3): 355-366.

Weber, J., "Immunotherapy for Melanoma," *Curr. Opin. Oncol.*, Mar. 2011, 23(2): 163-169.

Wolchok, J.D. et al, "Guidelines for the Evaluation of Immune Therapy Activity in Solid Tumors: Immune-Related Response Criteria," *Clinical Cancer Research* (American Association for Cancer Research), Dec. 2009, 15(23): 7412-7420.

Puzanov, M. Milhem, R.H.I. Andtbacka, D. Minor, O. Hamid, A. Li, J. Chou, H. Kaufman, Jun. 26, 2015. Results and Interpretations of ASCO Presentations 2015: Interdisciplinary Global Conference on News in Melanoma/Skin Cancer. *5th European Post-Chicago Melanoma/Skin Cancer Meeting*. Leonardo Royal Hotel, Munich, Germany.

(56) References Cited

OTHER PUBLICATIONS

Kaufman, Howard L. Combination Immunotherapy for Melanoma, Clinical Review & Education from the JAMA Network, pp. 387-388, JAMA Oncology, Jun. 2015, vol. 1, No. 3.

Hodi, Stephen, F. Sargramostim plus Ipilimumab vs Ipilimumab Alone for Treatment of Metastatic Melanoma: A Randomized Clinical Trial, *JAMA*. Author manuscript; available in PMC Feb. 20, 2015, Published in final edited form as: *JAMA*. Nov. 5, 2014; 312(17): 1744-1753. doi:10.1001/jama.2014.13943, pp. 1-21.

Hoeller, Christopher, Systematic review of the use of granulocyte-macrophage colony-stimulating factor in patients with advanced melanoma, Cancer Immunol Immunother (2016) 65:1015-1034, DOI 10.1007/s00262-016-1860-3.

Kwek, Serena S. GM-CSF and ipilimumab therapy in metastatic melanoma: Clinical outcomes and immunologic responses, Oncoimmunology 2016, vol. 5, No. 4, e1101204 (10 pages), http://dx.doi.org/10.1080/2162402X.2015.1101204.

Luke, Jason J. Single Institution Experience of Ipilimumab 3 mg/kg with Sargramostim (GM-CSF) in Metastatic Melanoma, *Cancer Immunol Res*. Author manuscript; available in PMC Sep. 1, 2016, Published in final edited form as: *Cancer Immunol Res*. Sep. 2015; 3(9): 986-991. doi:10.1158/2326-6066.CIR-15/0066.

Goldberg, John, Biologic Activity of Autologous, Granulocyte-Macrophage Colony Stimulating Factor Secreting Alveolar Soft Parts Sarcoma and Clear Cell Sarcoma Vaccines, *Clin Cancer Res*. Author manuscript; available in PMC Jul. 15, 2016, Published in final edited form as: *Clin Cancer Res*. Jul. 15, 2015; 21(14): 3178-3186. doi:10.1158/1078-0432.CCR-14-2932.

Jaffee, Elizabeth M. Novel Allogeneic Granulocyte-Macrophage Colony-Stimulating Factor-Secreting Tumor Vaccine for Pancreatic Cancer: A Phase I Trial of Safety and Immune Activation, Journal of Clinical Oncology, vol. 19, No. 1 (Jan. 1, 2001): pp. 145-156.

Laheru, Dan, Allogeneic GM-CSF Secreting Tumor Immunotherapy (GVAX®)Alone or in Sequence with Cyclophosphamide for Metastatic Pancreatic Cancer: A Pilot Study of Safety, Feasibility and Immune Activation, *Clin Cancer Res*. Author manuscript; available in PMC Jun. 1, 2010, Published in final edited form as: *Clin Cancer Res*. Mar. 1, 2008; 14(5): 1455-1463. doi:10.1158/1078-0432.CCR-7-0371.

Le, Dung T., Evaluation of Ipilimumab in combination with allogeneic pancreatic tumor cells transfected with a GM-CSF gene in previously treated pancreatic cancer, J Immunother. Author manuscript; available in PMC Sep. 1, 2014, J Immunother. Sep. 2013; 36(7): 382-389. doi:10.1097/CJI.0b013e31829fb7a2.

Le, Dung T., Safety and Survival With GVAX Pancreas Prime and *Listeria Monocytogenes*—Expressing Mesothelin (CRS-207) Boost Vaccines for Metastatic Pancreatic Cancer, Journal of clinical Oncology, vol. 33, No. 12, Apr. 20, 2015, pp. 1325-1333.

Lipson Evan J., Safety and immunologic correlates of Melanoma GVAX, a GM-CSF secreting allogeneic melanoma cell vaccine administered in the adjuvant setting, *J Transl Med* (2015) 13:214, DOI 10.1186/s12967-015-0572-3.

Nemunaitis J., Phase 1/2 trial of autologous tumor mixed with an allogeneic GVAXs vaccine in advanced-stage non-small-cell lung cancer, Cancer Gene Therapy (2006) 13, 555-562.

Soares, Kevin C. PD-1/PD-L1 blockade together with vaccine therapy facilitates effector T cell infiltration into pancreatic tumors, *J Immunother*. Author manuscript; available in PMC Jan. 1, 2016, *J Immunother*. Jan. 2015; 38(1): 1-11. doi:10.1097/CJI. 0000000000000062.

Geary, Sean M., Prostate cancer vaccines Update on clinical development, OncoImmunology 2:5, e24523; May 201, pp. 1-8.

Komenaka, Ian, et al., Immunotherapy for Melanoma, Clinics in Dermatology 2004;22:251-265.

Grilley-Olson, Juneko E. et al., A dose-escalation phase I study of oral pan-CDK inhibitor Bay 1000394 in patients with advanced solid tumors: Dose escalation with an intermittent 28 days on/14 days off schedule., Journal of Clinical Oncology, May 20, 2012, vol. 30, No. 15, suppl. pt. 1, 3046.

\* cited by examiner

METHOD FOR TREATING MELANOMA USING A HERPES SIMPLEX VIRUS AND AN IMMUNE CHECKPOINT INHIBITOR

CROSS REFERENCE TO RELATED APPLICATIONS

This application is a national stage application under 35 U.S.C. § 371 of International Application No. PCT/US2013/057542, having an international filing date of Aug. 30, 2013, which claims the benefit of U.S. provisional patent application No. 61/694,963, filed Aug. 30, 2012, and U.S. provisional patent application No. 61/846,147, filed Jul. 15, 2013, all of which are incorporated herein by reference.

BACKGROUND

Melanoma is a tumor of melanocytes, cells that are derived from the neural crest. Although most melanomas arise in the skin, they may also arise from mucosal surfaces or at other sites to which neural crest cells migrate. Melanoma occurs predominantly in adults, and more than half of the cases arise in apparently normal areas of the skin. Early signs in a naevus that would suggest malignant change include darker or variable discoloration, itching, an increase in size, or the development of satellites. Ulcerations or bleeding are later signs. Melanoma in women occurs more commonly on the extremities and in men on the trunk or head and neck, but it can arise from any site on the skin surface.

Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Microscopic satellites in stage I melanoma may be a poor prognostic histologic factor, but this is controversial (Leon et al., Archives of Surgery 126(2): 1461-1468, 1991). Melanomas arising on the extremities or in women seem to have a better prognosis (Blois et al., Cancer 52(7): 1330-1341, 1983; Clark et al., J. National Cancer Inst. 81(24): 1893-1904, 1989; Slingluff et al., Cancer 70(7): 1917-1927, 1992; Koh, NEJM 325(3): 171-182, 1991; Shumate et al., Am J Surgery 162(4): 315-319, 1991). Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematological routes to distant sites. Any organ may be involved by metastases, but lungs and liver are common sites. The risk of relapse may decrease substantially over time, although late relapses are not uncommon.

Melanoma that has not spread beyond the initial site is highly curable. Most of these cases are those tumors that have not invaded beyond the papillary dermis (State II; thickness, 1.0 mm or less). Melanoma that has spread to regional lymph nodes (Stage III) may be curable with wide (2 to 4 cm) excision of the primary tumor and removal of the involved regional lymph nodes (Karakousis et al, Ann Surg Oncol 13: 533-541, 2006; Batch et al, J Clin Oncol. 27(36): 6199-6206, 2009). Melanoma that has spread to distant sites (Stage IV) is infrequently curable with standard therapy, although ipilimumab and vemurafenib both offer survival benefits, and long-term survival is occasionally achieved by resection of metastasis (Overett and Shiu, Cancer 56:1222-1230, 1985).

Melanoma is the fifth most common cancer in men and the sixth most common cancer in women in the United States of America (USA), with an estimated 76,250 new cases and 9,180 deaths expected in 2012 (Siegel et al., CA Cancer J Clin. 62(1): 10-29, 2102). In Europe, the annual incidence of melanoma is somewhat lower than that in the USA, at approximately 7 per 100,000 as compared to 18 per 100,000 in the USA (Ries et al, 2000). In Europe, approximately 83,729 new cases were diagnosed in 2008 and approximately 85,086 new cases were expected in 2010 (GLOBOCAN 2008, 2010). The incidence of melanoma is increasing rapidly worldwide, with a 270% increase in the USA between 1973 and 2002. This increase is the most rapid of any cancer with the exception of lung cancer in women (Jemal et al., CA Cancer J Clin. 56: 106-130, 2006; Ries et al., Cancer 88: 2398-2424, 2000).

Traditional nonsurgical therapies for unresectable or advanced melanoma in adults include, chemotherapy (Dacarbazine, temozolomide, or other agents either alone or in combination), or interleukin-2. Although some regimes produced objective responses, they were usually short-lived. New therapies such as BRAF inhibition (vemurafenib) and immune stimulatory agents (ipilimumab) have shown significant improvement in overall survival compared to control treatments for a limited percentage of patients treated, however toxicity is an issue.

Despite these efforts melanoma is increasing rapidly worldwide. There is a need for additional melanoma treatments. The present invention addresses this need and others.

SUMMARY OF THE INVENTION

The invention provides a method for the treatment of melanoma comprising administering to a patient with stages IIIb to IV melanoma an effective amount of an immune checkpoint inhibitor and a herpes simplex virus, wherein the herpes simplex virus lacks functional ICP34.5 genes, lacks a functional ICP47 gene and comprises a gene encoding human GM-CSF. In one embodiment the administration of the herpes simplex virus precedes the administration of the immune checkpoint inhibitor. In another embodiment the checkpoint inhibitor is an anti-CTLA-4 antibody. In a related embodiment the anti-CTLA-4 antibody is ipilimumab. In another embodiment the anti-CTLA-4 antibody is tremelimumab. In another embodiment the checkpoint inhibitor is a PD1 blocker. In another embodiment the checkpoint inhibitor is a PD-L1 blocker. In another embodiment the checkpoint inhibitor is an anti-PD1 antibody. In another embodiment the checkpoint inhibitor is an anti-PD-L1 antibody. In another embodiment the PD1 blocker is nivolumab. In another embodiment the PD1 blocker is lambrolizumab. In another embodiment the PD1 blocker is nivolumab. In another embodiment the PD1 blocker is CT-011. In another embodiment the PD1 blocker is AMP-224. In another embodiment the PD-L1 blocker is BMS-936559. In another embodiment the checkpoint inhibitor is a LAG-3 inhibitor. In another embodiment the LAG-3 inhibitor is IMP321. In another embodiment the checkpoint inhibitor is a B7-H3 inhibitor. In another embodiment, the B7-H3 inhibitor is MGA271. In another embodiment the checkpoint inhibitor is a B7-H4 inhibitor. In another embodiment the checkpoint inhibitor is a TIM3 inhibitor. In another embodiment the herpes simplex virus is talimogene laherparepvec.

The invention provides a method for the treatment of melanoma comprising administering to a patient with stages IIIb to IV melanoma a herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of $10^8$ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus, and wherein the herpes simplex virus lacks functional ICP34.5 genes, lacks a functional ICP47 gene and comprises a gene encoding human GM-CSF. In one embodiment the administration of the herpes simplex virus precedes the administration of the anti-CTLA-4 antibody. In one embodiment the anti-CTLA-4 antibody is ipilimumab. In another embodiment the herpes simplex virus is talimogene laherparepvec.

The invention provides a method of promoting a combination treatment comprising a herpes simplex virus lacking functional ICP34.5 genes, lacking a functional ICP47 gene and comprises a gene encoding human GM-CSF and an immune checkpoint inhibitor, for the treatment of a patient with stages IIIb to IV melanoma. In one embodiment the immune checkpoint inhibitor is an anti-CTLA-4 antibody. In a related embodiment the anti-CTLA-4 antibody is ipilimumab. In another embodiment the anti-CTLA-4 antibody is tremelimumab. In another embodiment the checkpoint inhibitor is a PD1 blocker. In another embodiment the checkpoint inhibitor is a PD-L1 blocker. In another embodiment the checkpoint inhibitor is an anti-PD1 antibody. In another embodiment the checkpoint inhibitor is an anti-PD-L1 antibody. In another embodiment the PD1 blocker is nivolumab. In another embodiment the PD1 blocker is lambrolizumab. In another embodiment the PD1 blocker is nivolumab. In another embodiment the PD1 blocker is CT-011. In another embodiment the PD1 blocker is AMP-224. In another embodiment the PD-L1 blocker is BMS-936559. In another embodiment the checkpoint inhibitor is a LAG-3 inhibitor. In another embodiment the LAG-3 inhibitor is IMP321. In another embodiment the checkpoint inhibitor is a B7-H3 inhibitor. In another embodiment, the B7-H3 inhibitor is MGA271. In another embodiment the checkpoint inhibitor is a B7-H4 inhibitor. In another embodiment the checkpoint inhibitor is a TIM3 inhibitor. In another embodiment the treatment comprises administering to a patient with stages IIIb to IV melanoma the herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of $10^8$ PFU/mL at day 1 of week 4, and every 2 weeks thereafter until complete response, and the anti-CTLA-4 antibody administered intravenously at a dose of 3 mg/kg every 3 weeks for 4 infusions beginning after the third dose of the herpes simplex virus. In another embodiment the herpes simplex virus is talimogene laherparepvec. In yet another embodiment the promotion is by a package insert, wherein the package insert provides instructions to receive cancer treatment with a herpes simplex virus in combination with an immune checkpoint inhibitor. In another embodiment the promotion is by a package insert accompanying a formulation comprising the herpes simplex virus. In yet another embodiment the promotion is by written communication to a physician or health care provider. In another embodiment the promotion is by oral communication to a physician or health care provider.

In another embodiment the promotion is followed by the treatment of the patient with the herpes simplex virus.

The invention provides a method of instructing a patient with stages IIIb to IV melanoma by providing instructions to receive a combination treatment with a herpes simplex virus lacking functional ICP34.5 genes, lacking a functional ICP47 gene and comprising a gene encoding human GM-CSF and an immune checkpoint inhibitor to extend survival of the patient. In one embodiment the immune checkpoint inhibitor is an anti-CTLA-4 antibody. In another embodiment the anti-CTLA-4 antibody is tremelimumab. In another embodiment the checkpoint inhibitor is a PD1 blocker. In another embodiment the checkpoint inhibitor is a PD-L1 blocker. In another embodiment the checkpoint inhibitor is an anti-PD1 antibody. In another embodiment the checkpoint inhibitor is an anti-PD-L1 antibody. In another embodiment the PD1 blocker is nivolumab. In another embodiment the PD1 blocker is lambrolizumab. In another embodiment the PD1 blocker is nivolumab. In another embodiment the PD1 blocker is CT-011. In another embodiment the PD1 blocker is AMP-224. In another embodiment the PD-L1 blocker is BMS-936559. In another embodiment the checkpoint inhibitor is a LAG-3 inhibitor. In another embodiment the LAG-3 inhibitor is IMP321. In another embodiment the checkpoint inhibitor is a B7-H3 inhibitor. In another embodiment, the B7-H3 inhibitor is MGA271. In another embodiment the checkpoint inhibitor is a B7-H4 inhibitor. In another embodiment the checkpoint inhibitor is a TIM3 inhibitor. In one embodiment the treatment comprises administering to a patient with stages IIIb to IV melanoma a herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of $10^8$ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus. In a related embodiment the anti-CTLA-4 antibody is ipilimumab. In another embodiment the herpes simplex virus is talimogene laherparepvec.

The invention provides a kit comprising a herpes simplex virus lacking functional ICP34.5 genes, lacking a functional ICP47 gene and comprises a gene encoding human GM-CSF and a package insert or label with directions to treat stages IIIb to IV melanoma by using a combination of the herpes simplex virus and an immune checkpoint inhibitor. In one embodiment the immune checkpoint inhibitor is an anti-CTLA-4 antibody. In another embodiment the anti-CTLA-4 antibody is tremelimumab. In another embodiment the checkpoint inhibitor is a PD1 blocker. In another embodiment the checkpoint inhibitor is a PD-L1 blocker. In another embodiment the checkpoint inhibitor is an anti-PD-L1 antibody. In another embodiment the checkpoint inhibitor is an anti-PD1 antibody. In another embodiment the PD1 blocker is nivolumab. In another embodiment the PD1 blocker is lambrolizumab. In another embodiment the PD1 blocker is nivolumab. In another embodiment the PD1 blocker is CT-011. In another embodiment the PD-L1 blocker is AMP-224. In another embodiment the PD-L1 blocker is BMS-936559. In another embodiment the checkpoint inhibitor is a LAG-3 inhibitor. In another embodiment the LAG-3 inhibitor is IMP321. In another embodiment the checkpoint inhibitor is a B7-H3 inhibitor. In another embodiment, the B7-H3 inhibitor is MGA271. In another embodiment the checkpoint inhibitor is a B7-H4 inhibitor. In another embodiment the checkpoint inhibitor is a TIM3 inhibitor. In another embodiment the directions to treat stages IIIb to IV melanoma comprise instructions to administer to a patient with stages IIIb to IV melanoma a herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of $10^8$ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus. In a related embodiment the anti-CTLA-4 antibody is ipilimumab. In another embodiment the herpes simplex virus is talimogene laherparepvec. In a related embodiment is a method of manufacturing the kit as described above.

DETAILED DESCRIPTION OF THE INVENTION

The invention provides a method for the treatment of melanoma comprising administering to a patient with, stages IIIb to IV melanoma, an effective amount of an immune checkpoint inhibitor and a herpes simplex virus, wherein the herpes simplex virus lacks functional ICP34.5 genes, lacks a functional ICP47 gene and comprises a gene encoding human granulocyte macrophage colony stimulating factor (GM-CSF). Tumor cells are transfected by direct injection of the virus into accessible tumor lesions where the virus replicates in the tumor cells, bringing about tumor cell necrosis and the liberation of tumor antigens. Local expression of human GM-CSF induces local and distant immunological responses to the tumor antigens at both the injected and distant tumor deposits.

CTLA-4 is an immune checkpoint molecule that downregulates pathways of T-cell activation. CTLA-4 is a negative regulator of T-cell activation. Blockade of CTLA-4 has been shown to augment T-cell activation and proliferation. The combination of the herpes simplex virus and the anti-CTLA-4 antibody is intended to enhance T-cell activation through two different mechanisms in order to augment the anti-tumor immune response to tumor antigen released following the lytic replication of the virus in the tumor. Therefore, the combination of the herpes simplex virus and the anti-CTLA-4 antibody may enhance the destruction of the injected and un-injected/distal tumors, improve overall tumor response, and extend overall survival, in particular where the extension of overall survival is compared to that obtained using an anti-CTLA-4 antibody alone.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2 (Pardoll, Nature Reviews Cancer 12: 252-264, 2012). These proteins are responsible for co-stimulatory or inhibitory interactions of T-cell responses Immune checkpoint proteins regulate and maintain self-tolerance and the duration and amplitude of physiological immune responses. Immune checkpoint inhibitors include antibodies or are derived from antibodies.

As used herein, the term "antibody" includes reference to both glycosylated and non-glycosylated immunoglobulins of any isotype or subclass or to an antigen-binding region thereof that competes with the intact antibody for specific binding, unless otherwise specified, including monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, antibody derivatives, antibody analogues and fragments thereof, respectively. Also included are immunological fragments of an antibody (e.g., a Fab, a Fab', a F(ab')$_2$, or a scFv), irrespective of whether such antibodies are produced, in whole or in part, via immunization, through recombinant technology, by way of in vitro synthetic means, or otherwise. Thus, the term "antibody" is inclusive of those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such antibodies have variable and constant regions derived from germline immunoglobulin sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the $V_H$ and $V_L$ regions of the antibodies are sequences that, while derived from and related to the germline $V_H$ and $V_L$ sequences of a particular species (e.g., human), may not naturally exist within that species' antibody germline repertoire in vivo. Unless otherwise indicated, the term "antibody" includes, in addition to antibodies comprising two full-length heavy chains and two full-length light chains, derivatives, variants, fragments, and muteins thereof. In some instances "antibody" may include fewer chains such as antibodies naturally occurring in camelids which may comprise only heavy chains.

As used herein, the terms "patient" or "subject" are used interchangeably and mean a mammal, including, but not limited to, a human or non-human mammal, such as a bovine, equine, canine, ovine, or feline. Preferably, the patient is a human.

As used herein, "objective response rate" is the incidence rate of either a confirmed complete response or partial response per the modified Immune-Related Response Criteria (irRC) (Wolchok et al, Clin Cancer Res, 15(23):7412-7420, 2009) incorporated herein in its entirety.

As used herein, "time to response" refers to the time from treatment to the date of the first confirmed objective response, per the modified irRC.

As used herein, "duration of response" is the time from first confirmed objective response to confirmed disease progression per the modified irRC or death, whichever occurs earlier.

As used herein, "progression free survival" is the time from treatment to the date of first of confirmed disease progression per modified irRC criteria.

As used herein, "survival" refers to the patient remaining alive, and includes overall survival as well as progression free survival. 1-year survival rate and 2-year survival rate refers to the K-M estimate of the proportion of subjects alive at 12 month or 24 months.

By "extending survival" is meant increasing overall survival and/or progression free survival in a treated patient relative to a control treatment protocol, such as treatment with only ipilimumab. Survival is monitored for at least about one month, two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

For the methods of the invention, the term "instructing" a patient means providing directions for applicable therapy, medication, treatment, treatment regimens, and the like, by any means, but preferably in writing. Instructing can be in the form of prescribing a course of treatment, or can be in the form of package inserts or other written promotional material.

For the methods of the invention, the term "promoting" means offering, advertising, selling, or describing a particular drug, combination of drugs, or treatment modality, by any means, including writing, such as in the form of package inserts. Promoting herein refers to promotion of therapeutic agent(s), such as a herpes simplex virus, wherein the herpes simplex virus lacks functional ICP34.5 genes, lacks a functional ICP47 gene and comprises a gene encoding human GM-CSF, for an indication, such as melanoma treatment, where such promoting is authorized by the Food and Drug Administration (FDA) as having been demonstrated to be associated with statistically significant therapeutic efficacy and acceptable safety in a population of subjects. Promotion also includes the combination of a herpes simplex virus, wherein the herpes simplex virus lacks functional ICP34.5 genes, lacks a functional ICP47 gene and comprises a gene encoding human GM-CSF in combination with an immune checkpoint inhibitor for an indication, such as melanoma treatment.

The term "marketing" is used herein to describe the promotion, selling or distribution of a product (e.g., drug). Marketing specifically includes packaging, advertising and any business activity with the purpose of commercializing a product.

The invention provides a herpes simplex virus (HSV) which lacks functional ICP34.5 genes, lacks a functional ICP47 gene and comprises a gene encoding human GM-CSF. In one embodiment the herpes simplex virus is HSV-1. The ICP34.5 gene is located in the terminal repeats of the long region of HSV and therefore there are two copies per genome. Previous studies have shown that functional deletion of the neurovirulence gene, ICP34.5, renders the virus avirulent. The ICP47 gene is located in the unique short region of HSV. The ICP47 gene product interacts with the transporter associated with antigen processing (TAP1 and TAP2) and blocks antigen processing via MHC class I molecules. Deletion of the ICP47 gene allows greater antigen processing within infected cells and is intended to result in a concomitant increase in the immune response to infected cells. GM-CSF is a cytokine known to be involved in the stimulation of immune responses. Using homologous recombination with plasmid DNA, heterologous genes, such as that encoding human GM-CSF, can be inserted into the HSV viral genome, and viral genes, such as ICP34.5 and ICP47, can be functionally deleted. In one embodiment, the herpes simplex virus is talimogene laherparepvec.

Talimogene laherparepvec, HSV-1 [strain JS1] ICP34.5-/ICP47-/hGM-CSF, (previously known as OncoVEX$^{GM-CSF}$), is an intratumorally delivered oncolytic immunotherapy comprising an immune-enhanced HSV-1 that selectively replicates in solid tumors. (Lui et al., Gene Therapy, 10:292-303, 2003; U.S. Pat. No. 7,223,593 and U.S. Pat. No. 7,537,924). The HSV-1 was derived from Strain JS1 as deposited at the European collection of cell cultures (ECAAC) under accession number 01010209. In talimogene laherparepvec, the HSV-1 viral genes encoding ICP34.5 have been functionally deleted. Functional deletion of ICP34.5, which acts as a virulence factor during HSV infection, limits replication in non-dividing cells and renders the virus non-pathogenic. The safety of ICP34.5-functionally deleted HSV has been shown in multiple clinical studies (MacKie et al, Lancet 357: 525-526, 2001; Markert et al, Gene Ther 7: 867-874, 2000; Rampling et al, Gene Ther 7:859-866, 2000; Sundaresan et al, J. Virol 74: 3822-3841, 2000; Hunter et al, J Virol August; 73(8): 6319-6326, 1999). In addition, ICP47 (which blocks viral antigen presentation to major histocompatibility complex class I and II molecules) has been functionally deleted from talimogene laherparepvec. Functional deletion of ICP47 also leads to earlier expression of US11, a gene that promotes virus growth in tumor cells without decreasing tumor selectivity. The coding sequence for human GM-CSF, a cytokine involved in the stimulation of immune responses, has been inserted into the viral genome of talimogene laherparepvec. The insertion of the gene encoding human GM-CSF is such that it replaces nearly all of the ICP34.5 gene, ensuring that any potential recombination event between talimogene laherparepvec and wild-type virus could only result in a disabled, non-pathogenic virus and could not result in the generation of wild-type virus carrying the gene for human GM-CSF. The HSV thymidine kinase (TK) gene remains intact in talimogene laherparepvec, which renders the virus sensitive to anti-viral agents such as acyclovir. Therefore, acyclovir can be used to block talimogene laherparepvec replication, if necessary.

Talimogene laherparepvec produces a direct oncolytic effect by replication of the virus in the tumor, and induction of an anti-tumor immune response enhanced by the local expression of GM-CSF. Since melanoma is a disseminated disease, this dual activity is beneficial as a therapeutic treatment. The intended clinical effects include the destruction of injected tumors, the destruction of local, locoregional, and distant uninjected tumors, a reduction in the development of new metastases, a reduction in the rate of overall progression and of the relapse rate following the treatment of initially present disease, and prolonged overall survival.

Talimogene laherparepvec has been tested for efficacy in a variety of in vitro (cell line) and in vivo murine tumor models and has been shown to eradicate tumors or substantially inhibit their growth at doses comparable to those used in clinical studies. Nonclinical evaluation has also confirmed that GM-CSF enhances the immune response generated, enhancing both injected and uninjected tumor responses, and that increased surface levels of MHC class I molecules result from the deletion of ICP47. Talimogene laherparepvec has been injected into normal and tumor-bearing mice to assess its safety. In general, the virus has been well tolerated, and doses up to 1×10$^8$ PFU/dose have given no indication of any safety concerns. (See, for example, Liu et al., Gene Ther 10: 292-303, 2003)

Clinical studies have been or are being conducted in several advanced tumor types (advanced solid tumors, melanoma, squamous cell cancer of the head and neck, and pancreatic cancer), with over 400 subjects treated with talimogene laherparepvec (see, for example, Hu et al., Clin Can Res 12: 6737-6747, 2006; Harrington et al., J Clin Oncol. 27(15a): abstract 6018, 2009; Kaufman et al., Ann Surgic Oncol. 17: 718-730, 2010; Kaufman and Bines, Future Oncol. 6(6): 941-949, 2010). Clinical data indicate that talimogene laherparepvec has the potential to provide overall clinical benefit to patients with advanced melanoma. In particular, a high rate of complete response was achieved in stage Inc to IV melanoma (Scenzer et al., J. Clin. Oncol. 271(12):907-913, 2009). In addition, responses were observed in both injected and uninjected sites, including visceral sites.

The immune system has multiple inhibitory pathways that are critical for maintaining self-tolerance and modulating immune responses. In T-cells, the amplitude and quality of response is initiated through antigen recognition by the T-cell receptor and is regulated by immune checkpoint proteins that balance co-stimulatory and inhibitory signals.

Cytotoxic T-lymphocyte associated antigen 4 (CTLA-4) is an immune checkpoint protein that down-regulates pathways of T-cell activation (Fong et al., Cancer Res. 69(2): 609-615, 2009; Weber Cancer Immunol Immunother, 58:823-830, 2009). Blockade of CTLA-4 has been shown to augment T-cell activation and proliferation Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells and thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CDLA-4 antibody is tremelimumab, (ticilimumab, CP-675,206). In one embodiment, the anti-CTLA-4 antibody is ipilimumab (also known as 10D1, MDX-D010) a fully human monoclonal IgG antibody that binds to CTLA-4. Ipilimumab is marketed under the name Yervoy™ and has been approved for the treatment of unresectable or metastatic melanoma.

Another immune checkpoint protein is programmed cell death 1 (PD-1). PD1 limits the activity of T cells in peripheral tissues at the time of an inflammatory response to infection and to limit autoimmunity PD1 blockade in vitro enhances T-cell proliferation and cytokine production in response to a challenge by specific antigen targets or by allogeneic cells in mixed lymphocyte reactions. A strong correlation between PD1 expression and response was shown with blockade of PD1 (Pardoll, Nature Reviews Cancer, 12: 252-264, 2012). PD1 blockade can be accomplished by a variety of mechanisms including antibodies that bind PD1 or its ligand, PDL1. Examples of PD1 and PDL1 blockers are described in U.S. Pat. Nos. 7,488,802; 7,943, 743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In certain embodiments the PD1 blockers include anti-PD-L1 antibodies. In certain other embodiments the PD1 blockers include anti-PD1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD1; AMP-224 is a fusion protein of B7-DC; an antibody Fc portion; BMS-936559 (MDX-1105-01) for PD-L1 (B7-H1) blockade.

Other immune-checkpoint inhibitors include lymphocyte activation gene-3 (LAG-3) inhibitors, such as IMP321, a soluble Ig fusion protein (Brignone et al., 2007, J. Immunol 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94).

Without wishing to be bound by any theory of the invention, in one embodiment the combination of a herpes simplex virus, wherein the herpes simplex virus lacks functional ICP34.5 genes, lacks a functional ICP47 gene and comprises a gene encoding human GM-CSF and an immune checkpoint inhibitor, may increase the magnitude of tumor specific T cell responses as compared to ipilimumab alone in patients, this effect can be particularly observed with previously untreated, unresectable, stable IIIb-IV melanoma. The combination is intended to enhance the systemic anti-tumor response to tumor antigens following the lytic replication of talimogene laherparepvec in tumors. Therefore, the combination therapy may result in enhanced destruction of injected tumors as well as uninjected/distant tumors, including micrometastatic disease to improve the rate of overall tumor response and duration of response. Overall, these effects may contribute to an improvement in overall survival, particularly when compared to treatment using ipilimumab alone.

The use of talimogene laherparepvec in combination with an immune checkpoint inhibitor is intended to enhance T-cell activation through different mechanisms, respectively augmenting dendritic cell-mediated tumor antigen presentation (Kaufman et al., Ann Surg Oncol., 17(3):718-730, 2010) following the release of tumor antigens by lytic virus replication, enhanced through the local expression of GM-CSF, and antagonizing immune tolerance by blocking inhibitory signals mediated by a immune checkpoint inhibitor, such as CTLA-4, on T lymphocytes (Kapadia and Fong, J Clin Oncol., 23:8926-8928, 2005).

Monotherapy with talimogene laherparepvec has been shown to demonstrate a substantial proportion of responses and durable responses in a Phase 2 trial and is anticipated to demonstrate a clinically meaningful improvement in overall survival (Senzer et al, J Clin Oncol. 27(34):5763-5771, 2009). Ipilimumab monotherapy is known to provide a clinically meaningful but relatively modest increase in overall survival (approximately 2 to 3 months compared to dacarbazine or peptide vaccine), and complete and partial responses only occurred in a small subset of subjects (about 10.9%). Additionally, responses with ipilimumab often occurred late, with up to 10% of patients having responses after initial progression on therapy (Hodi et al, N Eng J Med., 363:711-723, 2010; Robert et al N Eng J Med., 364:2517-2526, 2011). This limits the utility of the agent in patients with relatively aggressive disease. Combination with talimogene laherparepvec can improve the time to response compared to use of ipilimumab alone.

The combination of a herpes simplex virus, wherein the herpes simplex virus lacks functional ICP34.5 genes, lacks a functional ICP47 gene and comprises a gene encoding human GM-CSF, and an immune checkpoint inhibitor is administered to patients with stage IIIb to stage IV melanoma. Melanoma stages are based on the TNM system developed by the American Joint Commission on Cancer (AJCC Cancer Staging Manual, Eds. Edge et al., Springer, 7$^{th}$ edition, 2010), incorporated herein in its entirety. The herpes simplex virus and the immune checkpoint inhibitor are formulated, dosed, and administered in a fashion consistent with good medical practice. In one embodiment talimogene laherparepvec is formulated in a buffer comprising 2% sorbitol, 4% inositol in phosphate buffer saline, pH 7.2.

Talimogene laherparepvec is administered by intratumoral injection into injectable cutaneous, subcutaneous, and nodal tumors at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. The recommended volume of talimogene laherparepvec to be injected into the tumor(s) is dependent on the size of the tumor(s) and should be determined according to the injection volume guideline in Table 1.

TABLE 1

Talimogene Laherparepvec Injection Volume Guidelines Based on Tumor Size

| Tumor Size (longest dimension) | Maximum Injection Volume |
| --- | --- |
| ≥5.0 cm | 4.0 ml |
| >2.5 cm to 5.0 cm | 2.0 ml |
| >1.5 cm to 2.5 cm | 1.0 ml |
| >0.5 cm to 1.5 cm | 0.5 ml |
| ≤0.5 cm | 0.1 ml |

All reasonably injectable lesions (cutaneous, subcutaneous and nodal disease that can be injected with or without ultrasound guidance) should be injected with the maximum dosing volume available on an individual dosing occasion. On each treatment day, prioritization of injections is recommended as follows: any new injectable tumor that has appeared since the last injection; by tumor size, beginning with the largest tumor; any previously uninjectable tumor(s) that is now injectable.

The immune checkpoint inhibitor is administered in the form of a composition comprising one or more additional components such as a physiologically acceptable carrier, excipient or diluent. The compositions may comprise one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with specific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. In one embodiment the immune checkpoint inhibitor is an anti-CTLA-4 antibody. In another embodiment the anti-CTLA-4 antibody is ipilimumab formulated at 5 mg/ml in 20 mM Tris HCl, 0.1 M sodium chloride, 0.1% w/v mannitol, 0.1 mM pentetic acid, 0.01% w/v polysorbate 80, pH 7.0. Further examples of components that may be employed in pharmaceutical formulations are presented in any Remington's Pharmaceutical Sciences including the 21$^{st}$ Ed. (2005), Mack Publishing Company, Easton, Pa.

Ipilimumab is administered intravenously over 90 (±15) minutes at a dose of 3 mg/kg every 3 weeks (±3 days) for 4 infusions beginning after the third dose of talimogene laherparpvec. When talimogene laherparepvec and ipilimumab are administered on the same day, talimogene laherparepvec must be administered first.

The duration of therapy will continue for as long as medically indicated or until a desired therapeutic effect (e.g., those described herein) is achieved. For example, patients can be treated with talimogene laherparepvec until complete response, all injectable tumors have disappeared, disease progression per the modified Immune-Related Response Criteria (irRC). Due to the mechanism of action, patients may experience growth in existing tumors or the appearance of new tumors prior to maximal clinical benefit of talimogene laherparepvec. Therefore, it is anticipated that dosing should be continued for at least 6 months from the time of initial dose provided that the subject has no evidence of clinically significant deterioration of health status requiring discontinuation of treatment and is able to tolerate the treatment. However, the course of treatment for any individual patient can be modified in clinical practice.

The invention provides a method for the treatment of melanoma comprising administering to a patient with stages IIIb to IV melanoma an effective amount of the immune checkpoint inhibitor and talimogene laherparepvec. The invention provides a method for the treatment of melanoma comprising administering to a patient with stages IIIb to IV melanoma an effective amount of an anti-CDLA4 antibody and talimogene laherparepvec. The invention provides a method for the treatment of melanoma comprising administering to a patient with stages IIIb to IV melanoma an effective amount of a PD1 blocker and talimogene laherparepvec. The invention provides a method for the treatment of melanoma comprising administering to a patient with stages IIIb to IV melanoma an effective amount of a PD-L1 blocker and talimogene laherparepvec. The invention provides a method for the treatment of melanoma comprising administering to a patient with stages IIIb to IV melanoma an effective amount of an anti-PD1 antibody and talimogene laherparepvec. The invention provides a method for the treatment of melanoma comprising administering to a patient with stages IIIb to IV melanoma an effective amount of an anti-PD-L1 antibody and talimogene laherparepvec. The invention provides a method for the treatment of melanoma comprising administering to a patient with stages IIIb to IV melanoma an effective amount of a TIM3 inhibitor and talimogene laherparepvec. The invention provides a method for the treatment of melanoma comprising administering to a patient with stages IIIb to IV melanoma an effective amount of a LAG-3 inhibitor and talimogene laherparepvec. The invention provides a method for the treatment of melanoma comprising administering to a patient with stages IIIb to IV melanoma an effective amount of a B7-H3 inhibitor and talimogene laherparepvec. The invention provides a method for the treatment of melanoma comprising administering to a patient with stages IIIb to IV melanoma an effective amount of a B7-H4 inhibitor and talimogene laherparepvec. The invention provides a method for the treatment of melanoma comprising administering to a patient with stages IIIb to IV melanoma an effective amount of the immune checkpoint inhibitor nivolumab and talimogene laherparepvec. The invention provides a method for the treatment of melanoma comprising administering to a patient with stages IIIb to IV melanoma an effective amount of the immune checkpoint inhibitor ipilimumab and talimogene laherparepvec. The invention provides a method for the treatment of melanoma comprising administering to a patient with stages IIIb to IV melanoma an effective amount of the immune checkpoint inhibitor tremelimumab and talimogene laherparepvec. The invention provides a method for the treatment of melanoma comprising administering to a patient with stages IIIb to IV melanoma an effective amount of the immune checkpoint inhibitor lambrolizumab and talimogene laherparepvec. The invention provides a method for the treatment of melanoma comprising administering to a patient with stages IIIb to IV melanoma an effective amount of the immune checkpoint inhibitor CT-011 and talimogene laherparepvec. The invention provides a method for the treatment of melanoma comprising administering to a patient with stages IIIb to IV melanoma an effective amount of the immune checkpoint inhibitor BMS-936559 and talimogene laherparepvec. The invention provides a method for the treatment of melanoma comprising administering to a patient with stages IIIb to IV melanoma an effective amount of the immune checkpoint inhibitor AMP-224 and talimogene laherparepvec. The invention provides a method for the treatment of melanoma comprising administering to a patient with stages IIIb to IV melanoma an effective amount of the immune checkpoint inhibitor IMP321 and talimogene laherparepvec. The invention provides a method for the treatment of melanoma comprising administering to a patient with stages IIIb to IV melanoma an effective amount of the immune checkpoint inhibitor MGA271 and talimogene laherparepvec.

Kits for use by medical practitioners comprising a herpes simplex virus, wherein the herpes simplex virus lacks functional ICP34.5 genes, lacks a functional ICP47 gene and comprises a gene encoding human GM-CSF and a package insert or label with direction to treat stages IIIb to IV melanoma in combination with an immune checkpoint inhibitor, such as an anti-CTLA-4 antibody. In one embodiment the treatment comprises administering to a patient with stages IIIb to IV melanoma a herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of $10^8$ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus. In one embodiment the anti-CTLA-4 antibody is ipilimumab. In another embodiment the herpes simplex virus is talimogene laherparepvec. In another embodiment the patient have previously untreated, unresectable, stages IIIb to IV melanoma. In another embodiment is provided a method of manufacturing the kit.

The invention provides a kit comprising talimogene laherparepvec and a package insert or label with directions to treat stages IIIb to IV melanoma by using a combination of talimogene laherparepvec and an immune checkpoint inhibitor. The invention provides a kit comprising talimogene laherparepvec and a package insert or label with directions to treat stages IIIb to IV melanoma by using a combination of talimogene laherparepvec and an anti-CTLA-4 antibody. The invention provides a kit comprising talimogene laherparepvec and a package insert or label with directions to treat stages IIIb to IV melanoma by using a combination of talimogene laherparepvec and a PD1 blocker. The invention provides a kit comprising talimogene laherparepvec and a package insert or label with directions to treat stages IIIb to IV melanoma by using a combination of talimogene laherparepvec and a PD-L1 blocker. The invention provides a kit comprising talimogene laherparepvec and a package insert or label with directions to treat stages IIIb to IV melanoma by using a combination of talimogene laherparepvec and an anti-PD-L1 antibody. The invention provides a kit comprising talimogene laherparepvec and a package insert or label with directions to treat stages IIIb to IV melanoma by using a combination of talimogene laherparepvec and an anti-PD1 antibody. The invention provides a kit comprising talimogene laherparepvec and a package insert or label with directions to treat stages IIIb to IV melanoma by using a combination of talimogene laherparepvec and TIM3 inhibitor. The invention provides a kit comprising talimogene laherparepvec and a package insert or label with directions to treat stages IIIb to IV melanoma by using a combination of talimogene laherparepvec and LAG-3 inhibitor. The invention provides a kit comprising talimogene laherparepvec and a package insert or label with directions to treat stages IIIb to IV melanoma by using a combination of talimogene laherparepvec and B7-H3 inhibitor. The invention provides a kit comprising talimogene laherparepvec and a package insert or label with directions to treat stages IIIb to IV melanoma by using a combination of talimogene laherparepvec and B7-H4 inhibitor. The invention provides a kit comprising talimogene laherparepvec and a package insert or label with directions to treat stages IIIb to IV melanoma by using a combination of talimogene laherparepvec and the immune checkpoint inhibitor ipilimumab. The invention provides a kit comprising talimogene laherparepvec and a package insert or label with directions to treat stages IIIb to IV melanoma by using a combination of talimogene laherparepvec and the immune checkpoint inhibitor tremelimumab. The invention provides a kit comprising talimogene laherparepvec and a package insert or label with directions to treat stages IIIb to IV melanoma by using a combination of talimogene laherparepvec and the immune checkpoint inhibitor nivolumab. The invention provides a kit comprising talimogene laherparepvec and a package insert or label with directions to treat stages IIIb to IV melanoma by using a combination of talimogene laherparepvec and the immune checkpoint inhibitor lambrolizumab. The invention provides a kit comprising talimogene laherparepvec and a package insert or label with directions to treat stages IIIb to IV melanoma by using a combination of talimogene laherparepvec and the immune checkpoint inhibitor CT-011. The invention provides a kit comprising talimogene laherparepvec and a package insert or label with directions to treat stages IIIb to IV melanoma by using a combination of talimogene laherparepvec and the immune checkpoint inhibitor AMP-224. The invention provides a kit comprising talimogene laherparepvec and a package insert or label with directions to treat stages IIIb to IV melanoma by using a combination of talimogene laherparepvec and the immune checkpoint inhibitor BMS-936559. The invention provides a kit comprising talimogene laherparepvec and a package insert or label with directions to treat stages IIIb to IV melanoma by using a combination of talimogene laherparepvec and the immune checkpoint inhibitor IMP321. The invention provides a kit comprising talimogene laherparepvec and a package insert or label with directions to treat stages IIIb to IV melanoma by using a combination of talimogene laherparepvec and the immune checkpoint inhibitor MGA271

Also provided is a method of promoting a combination treatment comprising a herpes simplex virus lacking functional ICP34.5 genes, lacking a functional ICP47 gene and comprising a gene encoding human GM-CSF, and an immune checkpoint inhibitor for the treatment of a patient with stages IIIb to IV melanoma. In one embodiment the immune checkpoint inhibitor is an anti-CTLA-4 antibody. In one embodiment the treatment comprises administering to a patient with IIIb to IV melanoma a herpes simplex virus administered by intratumoral injection into injectable cutaneous, subcutaneous, and nodal tumors at a dose of up to 4.0 ml of $10^6$ PFU/mL at day 1 of week 1 followed by a dose of up to 4.0 ml of 10⁸ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus. Promotion may be by package insert that provides instructions to receive cancer treatment with a herpes simplex virus lacking functional ICP34.5 genes, lacking a functional ICP47 gene and comprises a gene encoding human GM-CSF in combination with an immune checkpoint inhibitor. In one embodiment the immune checkpoint inhibitor is an anti-CTLA-4 antibody. In another embodiment the anti-CTLA-4 antibody is ipilimumab. In another embodiment the herpes simplex virus is talimogene laherparepvec. Promotion may be by written or oral communication with a physician or health care provider. In one embodiment the package insert is accompanied by a commercial formulation of the herpes simplex virus lacking functional ICP34.5 genes, lacking a functional ICP47 gene and comprises a gene encoding human GM-CSF and/or an immune checkpoint inhibitor. In another embodiment, promotion is followed by the treatment of the patient with the herpes simplex virus lacking functional ICP34.5 genes, lacking a functional ICP47 gene and comprises a gene encoding human GM-CSF in combination with an immune checkpoint inhibitor. In another embodiment the patient has previously untreated, unresectable, stages IIIb to IV melanoma.

The invention provides a method of promoting a combination treatment comprising talimogene laherparepvec and an immune checkpoint inhibitor, for the treatment of a patient with stages IIIb to IV melanoma. The invention provides a method of promoting a combination treatment comprising talimogene laherparepvec and an anti-CTLA-4 antibody, for the treatment of a patient with stages IIIb to IV melanoma. The invention provides a method of promoting a combination treatment comprising talimogene laherparepvec and PD1 blocker, for the treatment of a patient with stages IIIb to IV melanoma. The invention provides a method of promoting a combination treatment comprising talimogene laherparepvec and a PD-L1 blocker, for the treatment of a patient with stages IIIb to IV melanoma. The invention provides a method of promoting a combination treatment comprising talimogene laherparepvec and an anti-PD-L1 antibody, for the treatment of a patient with stages IIIb to IV melanoma. The invention provides a method of promoting a combination treatment comprising talimogene laherparepvec and an anti-PD1 antibody, for the treatment of a patient with stages IIIb to IV melanoma. The invention provides a method of promoting a combination treatment comprising talimogene laherparepvec and TIM3 inhibitor, for the treatment of a patient with stages IIIb to IV melanoma. The invention provides a method of promoting a combination treatment comprising talimogene laherparepvec and LAG-3 inhibitor, for the treatment of a patient with stages IIIb to IV melanoma. The invention provides a method of promoting a combination treatment comprising talimogene laherparepvec and B7-H3 inhibitor, for the treatment of a patient with stages IIIb to IV melanoma. The invention provides a method of promoting a combination treatment comprising talimogene laherparepvec and B7-H4 inhibitor, for the treatment of a patient with stages IIIb to IV melanoma. The invention provides a method of promoting a combination treatment comprising talimogene laherparepvec and the immune checkpoint inhibitor ipilimumab, for the treatment of a patient with stages IIIb to IV melanoma. The invention provides a method of promoting a combination treatment comprising talimogene laherparepvec and the immune checkpoint inhibitor nivolumab, for the treatment of a patient with stages IIIb to IV melanoma. The invention provides a method of promoting a combination treatment comprising talimogene laherparepvec and the immune checkpoint inhibitor lambrolizumab, for the treatment of a patient with stages IIIb to IV melanoma. The invention provides a method of promoting a combination treatment comprising talimogene laherparepvec and the immune checkpoint inhibitor CT-011, for the treatment of a patient with stages IIIb to IV melanoma. The invention provides a method of promoting a combination treatment comprising talimogene laherparepvec and the immune checkpoint inhibitor tremelimumab, for the treatment of a patient with stages IIIb to IV melanoma. The invention provides a method of promoting a combination treatment comprising talimogene laherparepvec and the immune checkpoint inhibitor AMP-224, for the treatment of a patient with stages IIIb to IV melanoma. The invention provides a method of promoting a combination treatment comprising talimogene laherparepvec and the immune checkpoint inhibitor BMS-936559, for the treatment of a patient with stages IIIb to IV melanoma. The invention provides a method of promoting a combination treatment comprising talimogene laherparepvec and the immune checkpoint inhibitor MDX-1105, for the treatment of a patient with stages IIIb to IV melanoma. The invention provides a method of promoting a combination treatment comprising talimogene laherparepvec and the immune checkpoint inhibitor IMP321, for the treatment of a patient with stages IIIb to IV melanoma. The invention provides a method of promoting a combination treatment comprising talimogene laherparepvec and the immune checkpoint inhibitor MGA271 for the treatment of a patient with stages IIIb to IV melanoma.

Also provided is a method of instructing a patient with stages IIIb to IV melanoma by providing instructions to receive a combination treatment with a herpes simplex virus lacking functional ICP34.5 genes, lacking a functional ICP47 gene and comprising a gene encoding human GM-CSF, and an immune checkpoint inhibitor, to extend survival of the patient, is also provided. In one embodiment the patient has previously untreated, unresectable, stages IIIb to IV melanoma. In one embodiment the treatment comprises administering to a patient with stages IIIb to IV melanoma a herpes simplex virus administered by intratumoral injection into injectable cutaneous, subcutaneous, and nodal tumors at a dose of up to 4.0 ml of 10⁶ PFU/mL at day 1 of week 1 followed by a dose of up to 4.0 ml of 10⁸ PFU/mL at day 1 of week 4, and every 2 weeks thereafter until complete response, and an anti-CTLA-4 antibody administered intravenously at a dose of 3 mg/kg every 3 weeks for 4 infusions beginning after the third dose of the herpes simplex virus. In one embodiment the immune checkpoint inhibitor is an anti-CTLA-4 antibody. In one embodiment the anti-CTLA-4 antibody is ipilimumab. In another embodiment the herpes simplex virus is talimogene laherparepvec.

The invention provides a method of instructing a patient with stages IIIb to IV melanoma by providing instructions to receive a combination treatment with talimogene laherparepvec and an immune checkpoint inhibitor to extend survival of the patient. The invention provides a method of instructing a patient with stages IIIb to IV melanoma by providing instructions to receive a combination treatment with talimogene laherparepvec and an anti-CDLA-4 antibody to extend survival of the patient. The invention provides a method of instructing a patient with stages IIIb to IV melanoma by providing instructions to receive a combination treatment with talimogene laherparepvec and a PD1 blocker to extend survival of the patient. The invention provides a method of instructing a patient with stages IIIb to IV melanoma by providing instructions to receive a combination treatment with talimogene laherparepvec and a PD-L1 blocker to extend survival of the patient. The invention provides a method of instructing a patient with stages IIIb to IV melanoma by providing instructions to receive a combination treatment with talimogene laherparepvec and an anti-PD1 antibody to extend survival of the patient. The invention provides a method of instructing a patient with stages IIIb to IV melanoma by providing instructions to receive a combination treatment with talimogene laherparepvec and an anti-PD-L1 blocker to extend survival of the patient. The invention provides a method of instructing a patient with stages IIIb to IV melanoma by providing instructions to receive a combination treatment with talimogene laherparepvec and a TIM3 inhibitor to extend survival of the patient. The invention provides a method of instructing a patient with stages IIIb to IV melanoma by providing instructions to receive a combination treatment with talimogene laherparepvec and a LAG-3 inhibitor to extend survival of the patient. The invention provides a method of instructing a patient with stages IIIb to IV melanoma by providing instructions to receive a combination treatment with talimogene laherparepvec and B7-H3 inhibitor to extend survival of the patient. The invention provides a method of instructing a patient with stages IIIb to IV melanoma by providing instructions to receive a combination treatment with talimogene laherparepvec and B7-H4 inhibitor to extend survival of the patient. The invention provides a method of instructing a patient with stages IIIb to IV melanoma by providing instructions to receive a combination treatment with talimogene laherparepvec and the immune checkpoint inhibitor ipilimumab to extend survival of the patient. The invention provides a method of instructing a patient with stages IIIb to IV melanoma by providing instructions to receive a combination treatment with talimogene laherparepvec and the immune checkpoint inhibitor tremelimumab to extend survival of the patient. The invention provides a method of instructing a patient with stages IIIb to IV melanoma by providing instructions to receive a combination treatment with talimogene laherparepvec and the immune checkpoint inhibitor nivolumab to extend survival of the patient. The invention provides a method of instructing a patient with stages IIIb to IV melanoma by providing instructions to receive a combination treatment with talimogene laherparepvec and the immune checkpoint inhibitor lambrolizumab to extend survival of the patient. The invention provides a method of instructing a patient with stages IIIb to IV melanoma by providing instructions to receive a combination treatment with talimogene laherparepvec and the immune checkpoint inhibitor CT-011 to extend survival of the patient. The invention provides a method of instructing a patient with stages IIIb to IV melanoma by providing instructions to receive a combination treatment with talimogene laherparepvec and the immune checkpoint inhibitor AMP-224 to extend survival of the patient. The invention provides a method of instructing a patient with stages IIIb to IV melanoma by providing instructions to receive a combination treatment with talimogene laherparepvec and the immune checkpoint inhibitor BMS-936559 to extend survival of the patient. The invention provides a method of instructing a patient with stages IIIb to IV melanoma by providing instructions to receive a combination treatment with talimogene laherparepvec and the immune checkpoint inhibitor IMP321 to extend survival of the patient. The invention provides a method of instructing a patient with stages IIIb to IV melanoma by providing instructions to receive a combination treatment with talimogene laherparepvec and the immune checkpoint inhibitor MGA271 to extend survival of the patient.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. All patents and other publications identified are expressly incorporated herein by reference in their entirety.

EXAMPLE

A Phase Ib/2 Open-label Evaluation of the Safety and Efficacy of Talimogene Laherparepvec and Ipilimumab Compared to Ipilimumab Alone in Subjects with Previously Untreated, Unresectable, Stage IIIb-IV Melanoma
Phase Ib The objective of this study was to determine the safety and tolerability of talimogene laherparepvec in combination with ipilimumab as assessed by incidence of dose-limiting toxicities (DLT) in subjects with previously untreated, unresectable, stages IIIb to IV melanoma. The study was an open-label, multi-center, single-arm, study. Talimogene laherparepvec in combination with ipilimumab will be administered to up to 18 subjects.

Talimogene laherparepvec was administered by intratumoral injection into injectable cutaneous, subcutaneous, and nodal tumors initially at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. Ipilimumab was administered intravenously at a dose of 3 mg/kg every 3 weeks (±3 days) for 4 infusions starting at day 1 of week 6 (ie, at the time of the third dose of talimogene laherparepvec), day 1 of week 9, day 1 of week 12, and day 1 of week 15. When talimogene laherparepvec and ipilimumab were administered on the same day, talimogene laherparepvec was administered first.

Subjects were treated with talimogene laherparepvec until complete response, all injectable tumors have disappeared, disease progression per the modified Immune-Related Response Criteria (irRC), or intolerance of study treatment, whichever occurs first.

Subjects were followed for safety approximately 30 (+7) days after the last dose of talimogene laherparepvec or 60 (+7) days after the last dose of ipilimumab, whichever was later, and will be followed for survival for approximately 24 months after the end of enrollment.

The result of this study was to demonstrate safety and tolerability of talimogene laherparepvec in combination with ipilimumab as assessed by incidence of dose-limiting toxicities (DTL) in subjects with previously untreated, unresectable, stages IIIb to IV melanoma.

Dose-limiting toxicities were defined as any grade (gr≥3 immune-related adverse event (AE) or gr≥4 AE of any etiology occurring between the first dose of ipilimumab and 6 weeks after. The incidence of DLTs was required to be ≤1 of the first 6 evaluable patients or ≤2 of the first 9 evaluable patients (if 2 DLTs were seen in the first 6 patients). Key entry criteria were previously untreated, unresectable Stage IIIB-IV melanoma, ECOG 0-1, measurable disease, and ≥1 injectable cutaneous, subcutaneous, or nodal tumor.

To date, 19 patients have been enrolled (13 patients received≥1 dose of talimogene laherparepvec or ipilimumab); 9 patients have completed the DLT period, 1 patient withdrew consent before receiving ipilimumab, and 9 patients have not yet reached the end of the DLT period. All DLT evaluable patients received at least 4 doses of talimogene laherparepvec and 2 doses of ipilimumab by the time of DLT cutoff (6 weeks post $1^{st}$ ipilimumab dose). No dose-limiting toxicities were observed in evaluable pts. Serious adverse events were reported in 1 of 19 patients to date (grade 3 nausea and abdominal distention in week 11 of treatment). Two partial responses were reported by week 12 in the 9 DLT evaluable patients.

The secondary objectives of this study include:

Estimating the efficacy of talimogene laherparepvec in combination with ipilimumab versus ipilimumab alone as determined by objective response rate (ORR).

Assessing the safety of talimogene laherparepvec in combination with ipilimumab as determined by incidence of all adverse event (AE)s, grade 3 AEs, serious adverse event (SAEs), and events requiring the discontinuation of study drug, local effects on the tumor (ie, pain, inflammation and ulceration), clinically significant laboratory changes, and clinically significant changes in vital signs not defined as DLT.

Phase 2

The primary objective of this study is to estimate the safety and efficacy of talimogene laherparepvec in combination with ipilimumab versus ipilimumab alone as assessed by overall survival (OS) in subjects with previously untreated, unresectable, stages IIIb to IV melanoma. The study is an open-label, multicenter, randomized study. Approximately 140 subjects are randomized 1:1 to receive the following:

arm 1: talimogene laherparepvec plus ipilimumab
arm 2: ipilimumab

Randomization is stratified by stage of disease (stage IIIb/c, stage IVM1a, and stage IVM1b vs. stage IVM1c) and BRAF V600E (mutation vs. mutation not present).

Talimogene laherparepvec is administered by intratumoral injection into injectable cutaneous, subcutaneous, and nodal tumors initially at a dose of up to 4.0 ml of $10^6$ PFU/mL at day 1 of week 1 followed by a dose of up to 4.0 ml of $10^8$ PFU/mL at day 1 of week 4, and every 2 weeks (±3 days) thereafter. Ipilimumab is administered intravenously at a dose of 3 mg/kg every 3 weeks (±3 days) for 4 infusions. Subjects randomized to arm 1 will receive ipilimumab starting at day 1 of week 6 (ie, at the time of the third dose of talimogene laherparepvec), day 1 of week 9, day 1 of week 12, and day 1 of week 15. When talimogene laherparepvec and ipilimumab are administered on the same day, talimogene laherparepvec is administered first. Subjects randomized to arm 2 receive ipilimumab starting at day 1 of week 1, day 1 of week 4, day 1 of week 7, and day 1 of week 10.

Subjects are treated with talimogene laherparepvec until complete response, all injectable tumors have disappeared, disease progression per the modified irRC, or intolerance of study treatment, whichever occurs first. Due to the mechanism of action, subjects may experience growth in existing tumors or the appearance of new tumors prior to maximal clinical benefit of talimogene laherparepvec. Therefore, dosing is continued for at least 6 months from the time of initial dose provided that the subject has no evidence of clinically significant deterioration of health status requiring discontinuation of treatment and is able to tolerate the treatment.

Subjects are followed for safety approximately 30 (+7) days after the last dose of talimogene laherparepvec or 60 (+7) days after the last dose of ipilimumab, whichever is later, and survival for approximately 24 months after the end of randomization.

The result of this study is to estimate the efficacy of talimogene laherparepvec in combination with ipilimumab versus ipilimumab alone as assessed by overall survival in subjects with previously untreated, unresectable, stages IIIb to IV melanoma. The result of the study is to measure the increase in magnitude of tumor specific T cell responses and the time to response compared to imilimumab alone.

The secondary objectives of this study include:

Estimating the efficacy of talimogene laherparepvec in combination with ipilimumab versus ipilimumab alone as determined by overall response rate, duration of response, time to response, progression free survival, resection rate, 1-year survival rate, and 2-year survival rate.

Assessing the safety of talimogene laherparepvec in combination with ipilimumab versus ipilimumab alone as determined by incidence of all adverse events (AEs), grade 3 AEs, SAEs, and events requiring the discontinuation of study drug, local effects on the tumor (ie, pain, inflammation and ulceration), clinically significant laboratory changes, and clinically significant changes in vital signs.

Inclusion criteria for both studies include the following:
1. Subject or subject's legally acceptable representative has provided informed consent
2. Histologically confirmed diagnosis of malignant melanoma
3. Stage IIIb, Inc, IVM1a, IVM1b, or IVM1c disease that is not suitable for surgical resection
4. Treatment naïve: Must not have received any prior systemic anticancer treatment consisting of chemotherapy, immunotherapy, or targeted therapy for unresectable stage IIIb to IV melanoma. Note: Subjects who received prior adjuvant therapy for melanoma will not be excluded. However, if the subject received adjuvant therapy, the subject must have completed therapy at least 6 months prior to enrollment (phase 1b) or randomization (phase 2). No prior talimogene laherparepvec, ipilimumab, other CTLA-4 inhibitors, programmed death-1 (PD-1) inhibitors, or tumor vaccine is allowed, even if given in the adjuvant setting.
5. Measurable disease defined as one or both of the following:
at least 1 melanoma lesion that can be accurately and serially measured in at least 2 dimensions and for which the longest diameter is ≥10 mm as measured by contrast-enhanced or spiral computed tomography (CT) scan for visceral or nodal/soft tissue disease (including lymph nodes)
at least 1≥5 mm superficial cutaneous or subcutaneous melanoma lesion as measured by calipers
6. Injectable disease (ie, suitable for direct injection or through the use of ultrasound [US] guidance) defined as follows:

at least 1 injectable cutaneous, subcutaneous, or nodal melanoma lesion ≥5 mm in longest diameter 7. Eastern Cooperative Oncology Group (ECOG) performance status 0 or 1
8. Male or female, age≥18 years
9. Adequate hematologic function as follows:
absolute neutrophil count (ANC)≥1.5×10$^9$/L
platelet count≥100×10$^9$/L
hemoglobin≥9 g/dL (without need for hematopoietic growth factor or transfusion support)
10. Adequate renal function as follows:
serum creatinine≤1.5×upper limit of normal (ULN), or 24-hour creatinine clearance ≥50 cc/min (Note: Creatinine clearance need not be determined if the baseline serum creatinine is within normal limits)
11. Adequate hepatic function as follows:
serum bilirubin≤1.5×ULN
aspartate amino transferase (AST)≤2.5×ULN
alanine amino transferase (ALT)≤2.5×ULN
12. Prothrombin time (PT)≤1.5×ULN (or international normalization ratio [INR]≤1.3) and partial thromboplastin time (PTT) or activated PTT (aPTT)≤1.5×ULN

The invention claimed is:

1. A method for the treatment of melanoma, said method comprising administering to a patient with stages IIIb to IV melanoma:
   (i) an effective amount of an anti-PD-1 antibody or anti-CTLA-4 antibody; and
   (ii) a herpes simplex virus, wherein said herpes simplex virus:
      lacks a functional ICP34.5 encoding gene;
      lacks a functional ICP47 encoding gene; and
      comprises a gene encoding human GM-CSF.

2. A kit comprising:
   (i) a herpes simplex virus, wherein said herpes simplex virus:
      lacks a functional ICP34.5 gene;
      lacks a functional ICP47 gene; and
      comprises a gene encoding human GM-CSF; and
   (ii) a package insert or label with directions to treat stages IIIb to IV melanoma by using a combination of the herpes simplex virus and an immune checkpoint inhibitor, wherein said immune checkpoint inhibitor is an anti-PD-1 or anti-CTLA-4 antibody.

3. A method for the treatment of melanoma, said method comprising administering to a patient with stages IIIb to IV melanoma:
   (i) a herpes simplex virus, wherein said herpes simplex virus:
      lacks a functional ICP34.5 gene;
      lacks a functional ICP47 gene; and
      comprises a gene encoding human GM-CSF, and
      wherein said herpes simplex virus is administered by intratumoral injection at a dose of up to 4.0 ml of 10$^6$ PFU/mL at day 1 of week 1 followed by a dose of up to 4.0 ml of 10$^8$ PFU/mL at day 1 of week 4, and every 2 weeks thereafter until complete response; and (ii) an anti-CTLA-4 antibody,
      wherein said anti-CTLA-4 antibody is administered intravenously at a dose of 3 mg/kg every 3 weeks for 4 infusions beginning after the third dose of said herpes simplex virus.

4. The method according to claim 1, wherein said anti-PD-1 antibody or anti-CTLA-4 antibody is an IgG antibody.
5. The method of claim 1, wherein the anti-CTLA-4 antibody is ipilimumab.
6. The method according to claim 1 or 4, wherein the administration of the herpes simplex virus precedes the administration of the anti-PD-1 or anti-CTLA-4 antibody.
7. The method according to claim 1 or 4, wherein the herpes simplex virus is talimogene laherparepvec.
8. The method according to claim 1, wherein the anti-PD-1 antibody is selected from the group consisting of nivolumab, lambrolizumab, CT-011, and AMP-224.
9. The kit according to claim 2, wherein the directions to treat stages IIIb to IV melanoma comprise instructions to administer to a patient with stages IIIb to IV melanoma:
   (i) a herpes simplex virus administered by intratumoral injection into injectable cutaneous, subcutaneous, and nodal tumors at a dose of up to 4.0 ml of 10$^6$ PFU/mL at day 1 of week 1 followed by a dose of up to 4.0 ml of 10$^8$ PFU/mL at day 1 of week 4, and every 2 weeks thereafter until complete response; and
   (ii) an anti-CTLA-4 antibody administered intravenously at a dose of 3 mg/kg every 3 weeks for 4 infusions beginning after the third dose of the herpes simplex virus.
10. A method of manufacturing the kit of claim 2.
11. The method according to claim 1, wherein:
said herpes simplex virus is talimogene laherparepvec; and
said anti-CTLA-4 antibody is ipilimumab.
12. The method according to claim 3, wherein:
said herpes simplex virus is talimogene laherparepvec; and
said anti-CTLA-4 antibody is ipilimumab.
13. The method according to claim 3 or 12, wherein said herpes simplex virus is administered by intratumoral injection into injectable cutaneous, subcutaneous, and nodal tumors.
14. The kit according to claim 2 or 9, wherein said anti-PD-1 antibody or anti-CTLA-4 antibody is an IgG antibody.
15. The method according to claim 1, wherein said anti-PD-1 antibody is lambrolizumab or nivolumab.
16. The method according to claim 1, wherein:
said herpes simplex virus is talimogene laherparepvec; and
said anti-PD-1 antibody is lambrolizumab or nivolumab.
17. The kit according to claim 2, wherein said anti-PD-1 antibody is lambrolizumab or nivolumab.
18. The kit according to claim 2, wherein:
said herpes simplex virus is talimogene laherparepvec; and
said anti-PD-1 antibody is lambrolizumab or nivolumab.
19. The kit according to claim 2, wherein:
said herpes simplex virus is talimogene laherparepvec; and
said anti-CTLA-4 antibody is ipilimumab.

* * * * *

Disclaimer

10,034,938 B2 - Ari Vanderwalde, Memphis, TN (US); Mohamed Shabooti, Agoura Hills, CA (US). METHOD FOR TREATING MELANOMA USING A HERPES SIMPLEX VIIRUS AND AN IMMUNE CHECKPOING INHIBITOR. Patent dated July 31, 2018. Disclaimer filed February 17, 2023, by the assignee, Amgen Inc.

I hereby disclaim the following complete claims 2, 10, 14, 17, 18 and 19, of said patent.

*(Official Gazette, May 2, 2023)*